(12) United States Patent   (10) Patent No.: US 8,781,203 B2
Davis et al.   (45) Date of Patent: *Jul. 15, 2014

(54) METHOD AND APPARATUS FOR DETERMINING AT LEAST ONE HEMOGLOBIN RELATED PARAMETER OF A WHOLE BLOOD SAMPLE

(71) Applicant: Abbott Point of Care, Inc., Princeton, NJ (US)

(72) Inventors: Graham Davis, Princeton, NJ (US); Stephen C. Wardlaw, Lyme, CT (US); Robert A. Levine, Guilford, CT (US); Darryn W. Unfricht, North Haven, CT (US); Niten Lalpuria, Mumbai (IN); Paul G. Mitsis, Trenton, NJ (US)

(73) Assignee: Abbott Point of Care, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/925,295

(22) Filed: Jun. 24, 2013

(65) Prior Publication Data

US 2014/0004554 A1   Jan. 2, 2014

Related U.S. Application Data

(62) Division of application No. 13/051,705, filed on Mar. 18, 2011, now Pat. No. 8,472,693.

(60) Provisional application No. 61/315,260, filed on Mar. 18, 2010.

(51) Int. Cl.
  *G06K 9/00*   (2006.01)
(52) U.S. Cl.
  USPC ......................................................... 382/134
(58) Field of Classification Search
  USPC ............................................ 382/134; 356/40
  See application file for complete search history.

(56) References Cited

U.S. PATENT DOCUMENTS 4,023,716 A   5/1977 Shapiro
4,066,361 A * 1/1978 Achter ............................ 356/41

(Continued)

FOREIGN PATENT DOCUMENTS

EP   0366151   5/1990
EP   1239284   9/2002

(Continued)

OTHER PUBLICATIONS

Sun et al, "Microminiaturized immunoassays using quantum dots as fluorescent label by laser confocal scanning fluorescence detection," Journal of Immunological Methods, Elsevier Science Publishers, vol. 249, No. 1-2, pp. 85-89, Mar. 2001.

(Continued)

*Primary Examiner* — Roy M Punnoose
(74) *Attorney, Agent, or Firm* — O'Shea Getz P.C.

(57) ABSTRACT

A method and apparatus for determining at least one hemoglobin related parameter of a whole blood sample is provided. The method includes the steps of: a) depositing the sample into an analysis chamber adapted to quiescently hold the sample for analysis, the chamber defined by an interior surface of a first panel, and an interior surface of a second panel, and the chamber has a height extending between the interior surfaces of the panels, wherein the chamber is configured to increase the oxygenation state of the sample to a substantially oxygenated state within a predetermined amount of time after entry into the chamber; b) imaging the at least one red blood cell contacting the interior surfaces, and producing image signals; c) determining an optical density of at least a portion of the imaged red blood cell contacting both interior surfaces; and d) determining the at least one hemoglobin related parameter of the red blood cell contacting the interior surfaces, using the determined optical density and a molar extinction coefficient for oxygenated hemoglobin.

17 Claims, 8 Drawing Sheets

(56) References Cited

U.S. PATENT DOCUMENTS

| | | | |
|---|---|---|---|
| 4,197,088 A | 4/1980 | Meserol et al. | |
| 4,487,081 A | 12/1984 | De Vaughn et al. | |
| 4,615,878 A | 10/1986 | Kass | |
| 5,012,818 A | 5/1991 | Joishy | |
| 5,068,181 A | 11/1991 | Driscoll | |
| 5,192,511 A | 3/1993 | Roach | |
| 5,284,771 A | 2/1994 | Fan et al. | |
| 5,447,838 A | 9/1995 | Meiklejohn et al. | |
| 5,454,268 A | 10/1995 | Kim | |
| 5,460,782 A | 10/1995 | Coleman et al. | |
| 5,739,042 A | 4/1998 | Frengen | |
| 5,768,407 A | 6/1998 | Shen et al. | |
| 5,770,160 A | 6/1998 | Smith et al. | |
| 5,851,835 A | 12/1998 | Groner | |
| 5,948,686 A | 9/1999 | Wardlaw | |
| 6,127,184 A | 10/2000 | Wardlaw | |
| 6,235,536 B1 | 5/2001 | Wardlaw | |
| 6,544,793 B2 | 4/2003 | Berndt | |
| 6,723,290 B1 | 4/2004 | Wardlaw | |
| 6,730,521 B1 | 5/2004 | Cassells | |
| 6,819,408 B1 | 11/2004 | Scrivens | |
| 6,866,823 B2 | 3/2005 | Wardlaw | |
| 6,929,953 B1 | 8/2005 | Wardlaw | |
| 7,731,901 B2 | 6/2010 | Wardlaw | |
| 7,850,916 B2 | 12/2010 | Wardlaw | |
| 7,903,241 B2 * | 3/2011 | Wardlaw et al. | 356/39 |
| 7,912,534 B2 * | 3/2011 | Grinvald et al. | 600/476 |
| 7,929,121 B2 | 4/2011 | Wardlaw | |
| 7,929,122 B2 * | 4/2011 | Wardlaw et al. | 356/40 |
| 7,951,599 B2 | 5/2011 | Levine | |
| 8,081,303 B2 * | 12/2011 | Levine et al. | 356/39 |
| 8,133,738 B2 | 3/2012 | Levine | |
| 8,310,658 B2 * | 11/2012 | Wardlaw et al. | 356/39 |
| 8,361,799 B2 | 1/2013 | Levine | |
| 8,472,693 B2 * | 6/2013 | Davis et al. | 382/134 |
| 2002/0028158 A1 * | 3/2002 | Wardlaw | 422/82.05 |
| 2002/0131902 A1 | 9/2002 | Levy | |
| 2003/0025896 A1 | 2/2003 | Oever et al. | |
| 2003/0224534 A1 | 12/2003 | Kawate | |
| 2004/0048330 A1 | 3/2004 | Bittner | |
| 2004/0165090 A1 | 8/2004 | Ning | |
| 2005/0002826 A1 | 1/2005 | Oguni et al. | |
| 2005/0026197 A1 | 2/2005 | Dertinger | |
| 2005/0277159 A1 | 12/2005 | Lehmann et al. | |
| 2006/0159962 A1 | 7/2006 | Chandler et al. | |
| 2006/0258018 A1 | 11/2006 | Curl et al. | |
| 2007/0087442 A1 * | 4/2007 | Wardlaw | 436/165 |
| 2007/0243117 A1 | 10/2007 | Wardlaw | |
| 2008/0070317 A1 | 3/2008 | Bradshaw et al. | |
| 2010/0015691 A1 | 1/2010 | Krogh | |
| 2011/0164803 A1 | 7/2011 | Wang | |

FOREIGN PATENT DOCUMENTS

| | | |
|---|---|---|
| GB | 2254414 | 10/1992 |
| WO | 9802727 | 1/1998 |
| WO | 0057891 | 5/2000 |
| WO | 0223154 | 3/2002 |

OTHER PUBLICATIONS

Goldman et al., "Multiplexed Toxin Analysis using Four Colors of Quantum Dot Fluororeagents," Analytical Chemistry, American Chemical Society, vol. 76, No. 3, pp. 684-688, Feb. 2004.

Matzdorff et al., "Quantitative assessment of platelets, platelet microparticles, and platelet aggregates in flow cytometry, "The Journal of Laboratory and Clinical Medicine, vol. 131, No. 6, pp. 507-517, Jun. 1998.

Hu Hu et al, "Effects of insulin on platelet and leukocyte activity in whole blood," Thrombosis Research, vol. 107, No. 5, pp. 209-215, Sep. 2002.

Sbrana et al., "Relationships between optical aggregometry (type born) and flow cytometry in evaluating ADP-induced platelet activation," Cytometry, Part B, Clinical Cytometry, vol. 74, No. 1, pp. 30-39, Jan. 2008.

Fishbane et al., "Reticulocyte hemoglobin content in the evaluation of iron status of hemodialysis patients", Kidney International, vol. 52, pp. 217-222, 1997.

Wray et al. "Characterization of the Near Infrared Absorption Spectra of Cytochrome aa3 and Haemoglobin for the Non-Invasive Monitoring of Cerebral Oxygenation", Biochimica et Ciophysica Acta, 933 (1988), 184-192.

Kim et al. "Engineering in Medicine and Biology: Extinction Coefficients of Hemoglobin for Near-Infrared Spectroscopy of Tissue", Mar./Apr. 2005.

Hematocrit/HCT and Calulated Hemoglobin/HB, Article 714178-00H, Rev. Date: Jun. 11, 2008.

Wood et al., "Resonance Raman Spectroscopy of Red Blood Cells Using Near-Infrared Laser Excitation", Analytical and Bioanalytical Chemistry, vol. 387, No. 5, Dec. 7, 2006, pp. 1691-1703.

Ellis et al., "Applicaton of Image Analysis for Evaluation of Red Blood Cell Dynamics in Capillaries", Microvascular Research, vol. 44, No. 2, Sep. 1, 1992, pp. 214-225.

Wan et al., "Contact Mechanics of a Thin-Walled Capsule adhered onto a Rigid planar Substrate", Medical & Biological Engineering & Computing 2001, vol. 39, p. 605-608.

Pfeifer, "Solder Bump Size and Shape Modeling and Experimental Validation", IEEE, 1997, 452-457.

* cited by examiner

METHOD AND APPARATUS FOR DETERMINING AT LEAST ONE HEMOGLOBIN RELATED PARAMETER OF A WHOLE BLOOD SAMPLE

The present application is a divisional of U.S. patent application Ser. No. 13/051,705 filed Mar. 18, 2011, which claims priority to U.S. Provisional Patent Application Ser. No. 61/315,260, filed Mar. 18, 2010.

BACKGROUND OF THE INVENTION

1. Technical Field

The present invention relates to apparatus and methods for analysis of blood samples in general, and for the determination of hemoglobin related parameters of a blood sample in particular.

2. Background Information

Physicians, veterinarians and scientists have examined human and animals' biologic fluids, especially blood, in order to determine constituent particulate quantities as well as to identify the presence of unusual particulates not seen in healthy subjects. The particulates generally measured, quantified and identified include red blood cells (RBCs), white blood cells (WBCs), and platelets. RBC analyses can include determinations of RBC number, size, volume, shape, hemoglobin content and concentration, and the hematocrit (also referred to as the packed cell volume). RBC analyses can also involve determining the presence and/or concentration of certain components within the red cells such as DNA, RNA, including the detection of the presence and/or enumeration of hematoparasites (e.g., malarial parasites) either in the RBCs or trypanosomes which are extracellular or leishmaniasis organisms which are in the WBCs as well as many other hematoparasites. WBC analyses can include a determination of the population frequency of WBC sub types generally referred to as a differential WBC count, as well as the notification of any unusual cell types not found in healthy subjects. Platelet (or in certain animals including birds, reptiles and fish, thrombocytes which are similar in function to platelets in mammals but are about ten times larger and nucleated) analyses can include platelet number, size, shape texture, and volume determinations, including determining the presence of clumps of platelets or thrombocytes within the sample.

The amount of information that can be determined by examining the blood of a human or animal is vast. It is particularly useful to determine the indices of RBCs; e.g., individual cell size, individual cell hemoglobin content and concentration, and population statistics of RBCs within a sample. The mean and dispersion statistics (e.g., coefficients of variation) for each of the aforementioned parameters can also provide important information, which has enabled physicians to better categorize disorders of RBCs.

Figure 1:
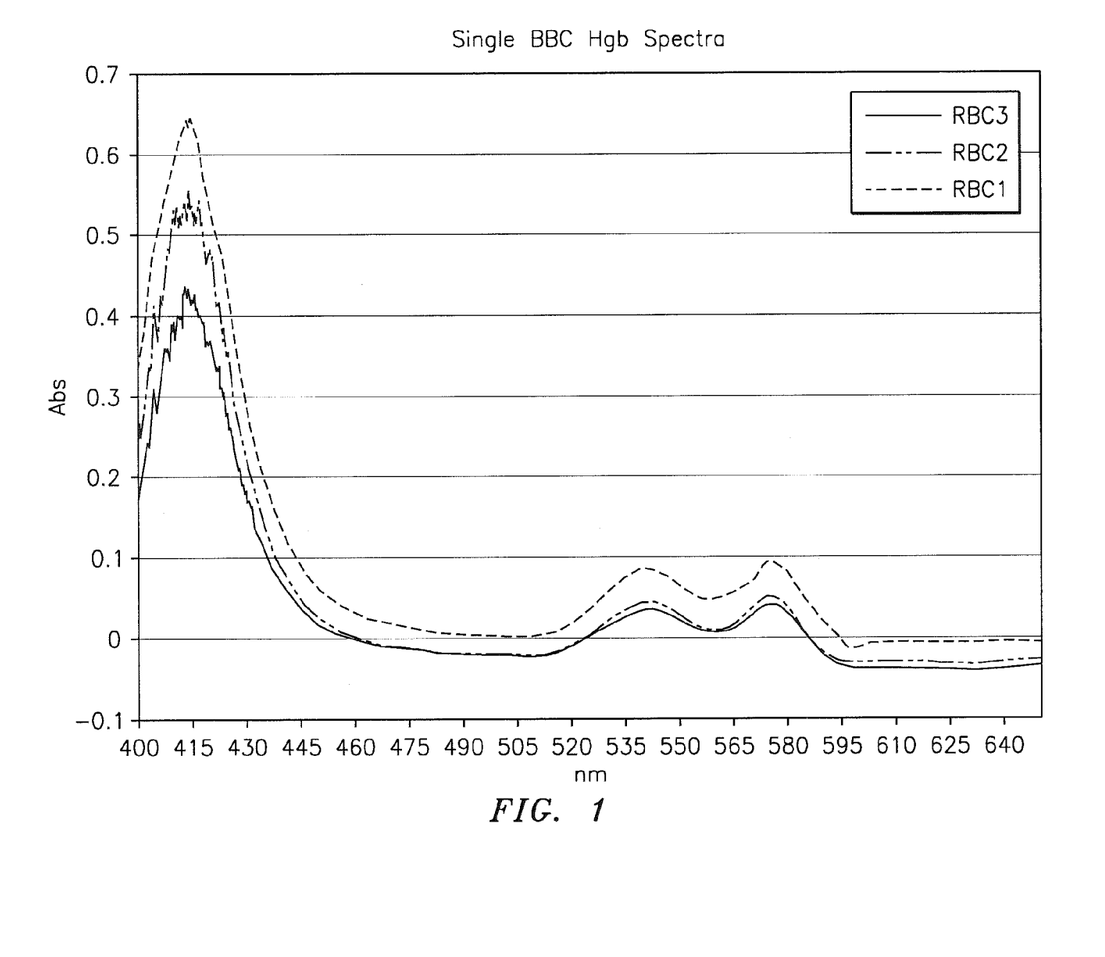
FIG. 1 is a chart of absorbance versus wavelength, for three separate RBCs.
Figure 2:
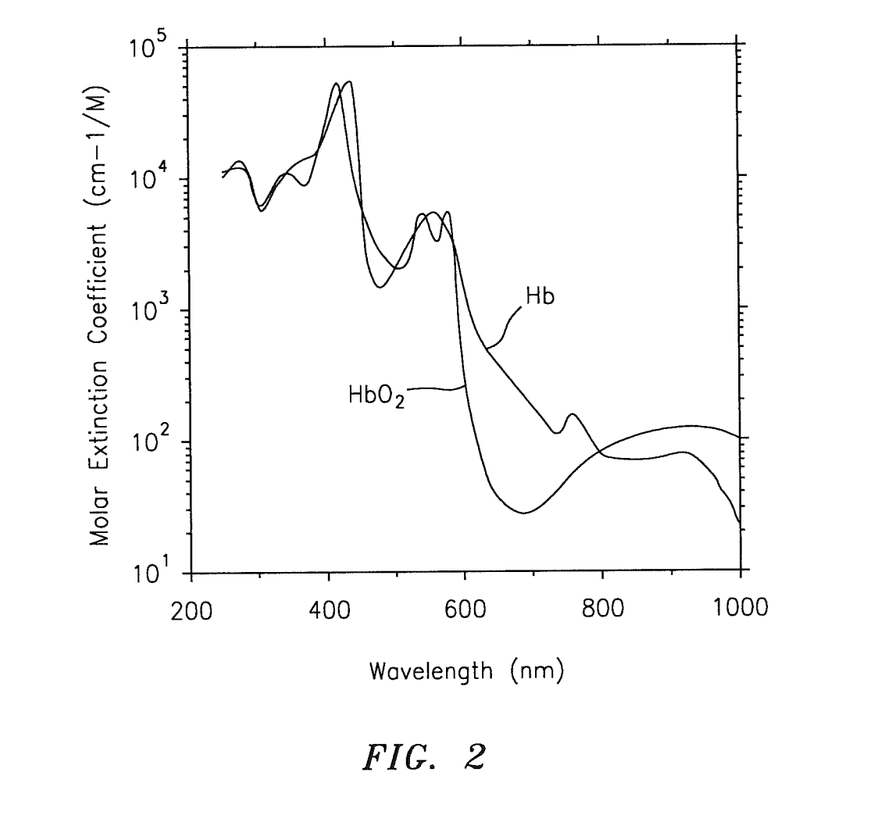
FIG. 2 is a graph of molar extinction coefficient versus wavelength for oxyhemoglobin ($HbO_2$) and deoxyhemoglobin (Hb).

Hemoglobinometry is very often performed on a sample by interrogating the sample with light. The amount of absorbance associated with hemoglobin varies considerably as a function of the wavelength of the interrogating light, as can be seen in FIG. 1, which illustrates absorbance versus wavelength for three separate RBCs. Hemoglobinometry is generally performed on precisely diluted blood, where the red blood cells are lysed and where the hemoglobin released from the lysed red blood cells is chemically modified (e.g., methods that convert it to cyanmethemoglobin or azo-methemoglobin) so that its molar extinction coefficient at wavelengths where hemoglobin has a significant and useful absorption are not affected by the ratio of oxyhemoglobin and deoxyhemoglobin. If the molar extinction coefficient is accurately known, the concentration of the hemoglobin in a sample can be accurately determined. In hemoglobin that is not chemically altered, however, the relative molar extinction coefficients of the spectra at useable wavelengths can differ by as much as 10 to 15 percent. For example, the graph shown in FIG. 2 shows the molar extinction coefficient for deoxyhemoglobin (Hb) and oxyhemoglobin ($HbO_2$) as a function of wavelength. It is clear from FIG. 2 that the absorbance spectrums for the two forms of hemoglobin (Hb, HbO2) differ significantly. Consequently, an error in the molar extinction coefficient value can introduce significant error into the calculations of related blood indices.

Prior art has addressed this problem by chemically modifying the blood sample, or by evaluating an unmodified blood sample using simultaneous equations for absorption over two different wavelengths, which adds expense and complexity to the process. The isosbestic points (i.e., points where the two species of hemoglobin have identical molar absorptivity) are not as sensitive or useful in clinical measurement due to their lack of flatness and relative low absorptivity.

SUMMARY OF THE INVENTION

To solve the analytical problems associated with the different molar extinction coefficients of deoxyhemoglobin and oxyhemoglobin, substantially oxygenated blood and substantially deoxygenated blood were separately evaluated. The term "substantially oxygenated" as used herein refers to blood having substantially more oxyhemoglobin than deoxyhemoglobin, which blood is characterized by a bright red color. The term "substantially deoxygenated" as used herein refers to blood having substantially more deoxyhemoglobin than oxyhemoglobin, which blood is characterized by a dark bluish color. During the evaluation, one portion of a blood sample was exposed to oxygen in a test tube for several minutes and gently rocked until the blood was bright red. The oxygenated blood was subsequently placed in an analysis apparatus and the hemoglobin concentration was determined. The deoxygenated blood was prepared by using the same venous blood source, filling a seven milliliter (7 ml) test tube with about 3.5 ml of blood and placing 100% nitrogen in space above it, stoppering the tube, and gently rocking the tube, replacing the gas above the blood with 100% nitrogen every five minutes. Within thirty minutes the blood was dark blue, which color is characteristic of deoxygenated blood. The samples of the deoxygenated and oxygenated blood yielded the same results for hemoglobin concentration utilizing the methods described below. The same test was performed on multiple blood sample and the results correlated at the 0.99 level with standard hemoglobinometry methods using cynamethemooglobin methodology performed on an Abbott Sapphire Hematology Analyzer.

The above investigation lead to the present invention improvement wherein a method and apparatus is provided for analyzing a sample of whole blood in which the sample is processed into a substantially oxygenated state, and the sample is analyzed as being in a substantially oxygenated state.

According to one aspect of the present invention, a method for determining at least one hemoglobin related parameter of a whole blood sample is provided. The method includes the steps of: a) depositing the sample into an analysis chamber adapted to quiescently hold the sample for analysis, the chamber defined by an interior surface of a first panel and an interior surface of a second panel, and the chamber has a height extending between the interior surfaces of the panels, wherein the chamber is configured to increase the oxygenation state of the sample to a substantially oxygenated state within a predetermined amount of time after entry into the chamber; b) imaging the at least one red blood cell contacting the interior surfaces, and producing image signals; c) determining an optical density of at least a portion of the imaged red blood cell contacting both interior surfaces; and d) determining the at least one hemoglobin related parameter of the red blood cell contacting the interior surfaces, using the determined optical density and a molar extinction coefficient for oxyhemoglobin.

According to another aspect of the present invention, an apparatus for determining at least one hemoglobin related parameter of a whole blood sample is provided. The apparatus includes an analysis chamber, an imaging unit, and a programmable analyzer. The analysis chamber is adapted to quiescently hold the whole blood sample. The chamber is defined by an interior surface of a first panel and an interior surface of a second panel. The chamber has a height extending between the interior surfaces of the panels. The chamber is configured to increase the oxygenation state of the sample to a substantially oxygenated state within a predetermined amount of time after entry into the chamber. The imaging unit includes an illuminator and an image dissector. The imaging unit is operable to image sample disposed within the chamber, and produce image signals representative of such imaged sample. The programmable analyzer is adapted to determine at least one hemoglobin related parameter of the sample, using the image signals and a molar extinction coefficient for oxyhemoglobin.

The advantages of our method over other methods of hemoglobinometry include: 1) lysis of the red blood cells is unnecessary; 2) chemical conversion of hemoglobin to cyanmethemoglobin or azo-hemoglobin is not required; 3) dilution of the blood is not required; and 4) the method can be performed on anticoagulated blood with no reagents other than the optional use of an isovolumetric sphering agent as described in the aforementioned patent application.

The present method and advantages associated therewith will become more readily apparent in view of the detailed description provided below, including the accompanying drawings.

DETAILED DESCRIPTION OF EMBODIMENTS OF THE INVENTION

The present method and apparatus for determining at least one hemoglobin related parameter of a whole blood sample allow a means for improving the accuracy of blood analyses. Analyzing a sample of substantially undiluted whole blood allows the determination of the red blood cell (RBC) cell volume (CV), mean cell volume (MCV), cell hemoglobin concentration (CHC), mean cell hemoglobin concentration (MCHC), and the mean cell hemoglobin content (MCH), as well as their population statistics, without the addition of any dyes, reagents (other than anticoagulants in some embodiments) or diluents to the sample.

The present method utilizes an analysis chamber that is operable to quiescently hold a sample of substantially undiluted anticoagulated whole blood for analysis. The chamber is typically sized to hold a relatively small amount of sample; i.e., about 0.2 to 1.0 µl of sample. The phrase "substantially undiluted" as used herein describes a blood sample which is either not diluted at all or has not been diluted purposefully, but has had some reagents added thereto for purposes of the analysis. To the extent the addition of the reagents dilutes the sample, if at all, such dilution has no clinically significant impact on the analysis performed. Typically, the only reagents that will be used in performing the present method are anticoagulants (e.g., EDTA, heparin) and in some instances an isovolumetric sphering agent. These reagents are generally added in dried form and are not intended to dilute the sample. Under certain circumstances (e.g., very rapid analysis), it may not be necessary to add the anticoagulating agent, but it is preferable to do so in most cases to ensure the sample is in a form acceptable for analysis. The term "quiescent" is used to describe that the sample is deposited within the chamber for analysis, and the sample is not purposefully moved relative to the chamber during the analysis; i.e., the sample resides quiescently within the chamber. To the extent that motion is present within the blood sample, it will predominantly be that due to Brownian motion of the blood sample's formed constituents, which motion is not disabling of the use of the device of this invention.

Figure 3:
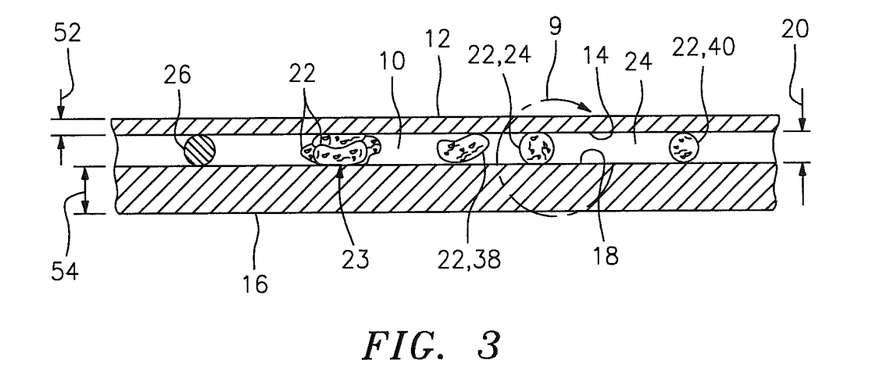
FIGS. 3-6 are cross-sectional diagrammatic representations of analysis chambers that may be used in the present method.
Figure 4:
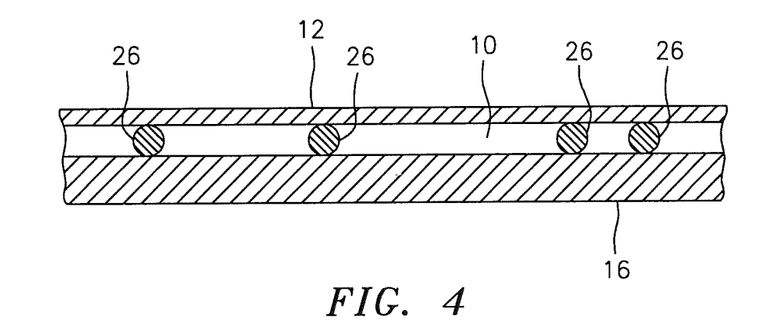

Now referring to FIG. 3, the analysis chamber 10 is defined by a first panel 12 having an interior surface 14, and a second panel 16 having an interior surface 18. In preferred embodiments, the panels 12, 16 are both sufficiently transparent to allow the transmission of light along predetermined wavelengths there through in an amount sufficient to perform the optical density analysis described below. At least a portion of the panels 12, 16 are parallel with one another, and within that portion the interior surfaces 14, 18 are separated from one another by a height 20 such that at least some individual RBCs 22 within a sample each individually contact both interior surfaces 14, 18, and/or one or more aggregates 23 of RBCs within the sample each contact both interior surfaces 14, 18 of the chamber panels 12, 16, and one or more RBC void areas (e.g., lacunae) 24 within the quiescent sample extend between the interior surfaces, as will be discussed in greater detail below. The preferred height of the chamber is in the range of 2-6 microns (i.e., 2-6 µm; $2-6\times10^{-6}$ m), and a chamber height of four microns (4µ) is particularly useful for analyzing RBCs. The chamber has a width and a length. For orientation purposes, the height may be considered to extend along a Z-axis, and the width and length defining an X-Y plane; e.g., width=X, and length=Y. In those instances where the chamber is not rectangular, the term "width" refers to the maximum width (i.e., "X") dimension of the chamber, and the term "length" refers to the maximum length (i.e., "Y") dimension of the chamber. The width and length of the chamber are at least one-thousand times greater than the height of the chamber; e.g., a chamber having a height of four microns (4µ) has a width and length of at least 4000 microns (i.e., each equal to or greater than 4 mm). The first and second panels 12, 16, also each have a thickness. In preferred embodiments, the first panel 12 (which can also be referred to as the "upper panel") has a thickness 52 that is less than the thickness 54 of the second panel 16 (which can also be referred to as the "lower panel"). The first panel 12 preferably has a thickness in the range of twenty to twenty-five microns (20-25µ). The second panel 16 preferably has a thickness of at least fifty microns (50µ). An advantage of the height versus width and length of the present chamber is that the chamber configures the relatively small volume of sample (e.g., about 0.2 to 1.0 µl) into a geometry that includes two substantial surface areas that facilitate the diffusion of oxygen into the sample to increase the percentage of oxyhemoglobin within the total hemoglobin of the sample. As is explained below, the increase in the oxyhemoglobin within the sample advantageously enables the use of the molar extinction coefficient for oxyhemoglobin alone.

Both the first and second panels 12, 16 are made of a polymer film; i.e., a polymer material in a planar configuration. The first panel 12 comprises a transparent material such as acrylic, polystyrene, polyethylene terphthalate (PET), and cyclic olefin copolymer (COC). In some embodiments, the first panel 12 is selected to be made of a material having a permeability that allows an amount of oxygen from ambient air to permeate through and diffuse into the sample residing within the chamber within a clinically reasonable period of time beginning with the time the sample is deposited within the chamber. The amount of air that permeates through the first panel 12 is adequate to detectably increase the oxygen state of the sample. In some embodiments, material of the first panel may possess sufficient oxygen solubility to permit an amount of oxygen disposed within the first panel to transfer from the panel 12 to the sample residing within the chamber within a clinically reasonable period of time beginning with the time the sample is deposited within the chamber. The amount of air that transfers from the first panel 12 is adequate to detectably increase the oxygen state of the sample. In these embodiments, the material of the upper panel 12 may provide the sole mechanism by which the amount of oxygen necessary to increase the oxygenation state of the sample to a substantially oxygenated state is provided, or they may provide a portion of that amount. An example of an acceptable commercially available material that be used to form the first panel 12 is DuPont® Melinex® 453 PET film.

Now referring to FIGS. 4-7, an example of an acceptable chamber 10 is shown that includes a first panel 12, a second panel 16, and at least three separators 26 disposed between the panels 12, 16. The separators 26 can be any structure that is disposable between the panels 12, 16, operable to space the panels 12, 16 apart from one another. The dimension 28 of a separator 26 that extends between the panels 12, 16 is referred to herein as the height 28 of the separator 26. The heights 28 of the separators 26 typically do not equal one another exactly (e.g., because of manufacturing tolerances), but are within commercially acceptable tolerance for spacing means used in similar analysis apparatus. Spherical beads are an example of an acceptable separator 26 and are commercially available from, for example, Bangs Laboratories of Fishers, Ind., U.S.A.

Figure 5:
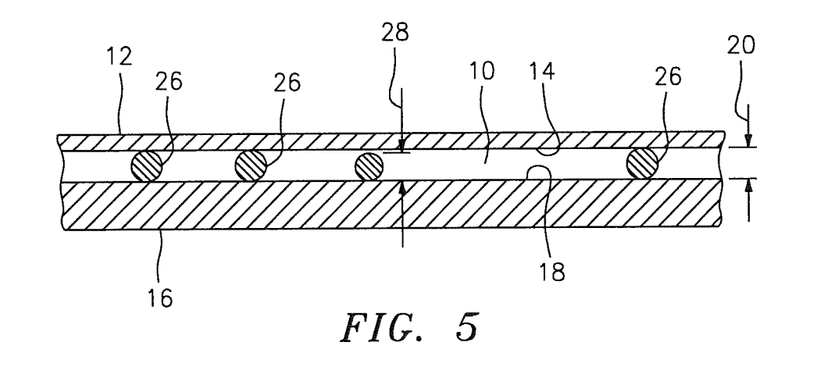
Figure 6:
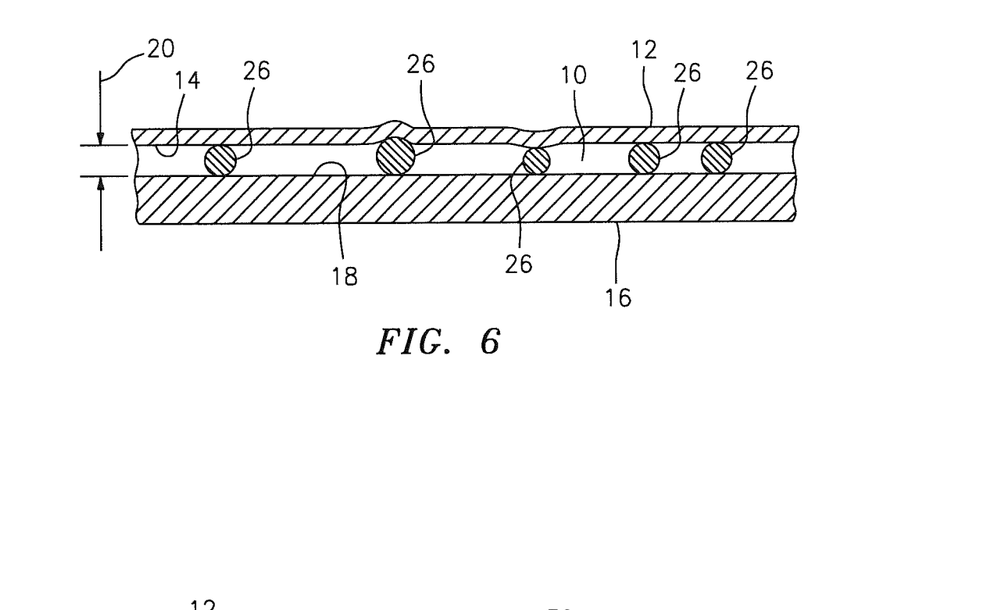
Figure 7:
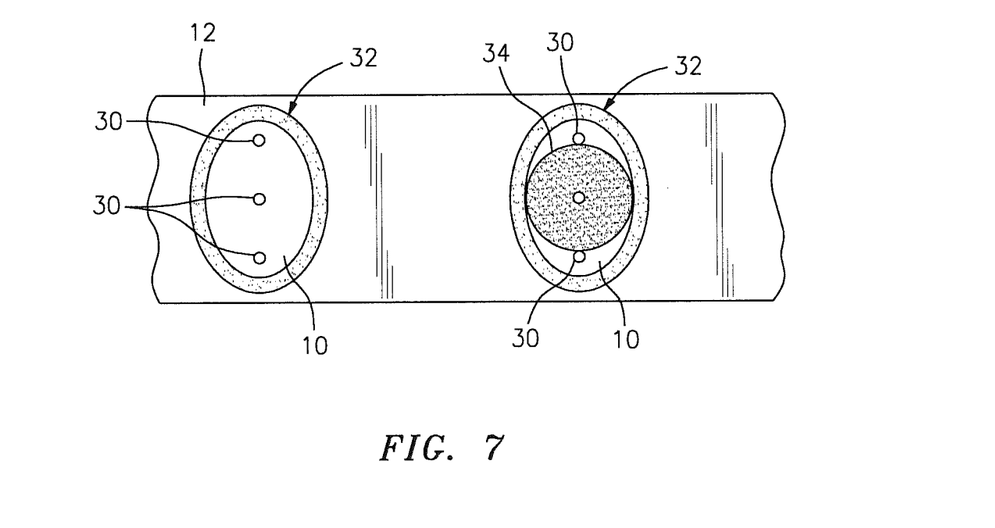
FIG. 7 is a diagrammatic planar view of a tape having a plurality of analysis chambers.

In the chamber embodiment shown in FIG. 3, the separators 26 consist of a material that has greater flexibility than one or both of the first panel 12 and the second panel 16. As can be seen in FIG. 5, the larger separators 26 are compressed to the point where most separators 26 are touching the interior surfaces 14, 18 of the panels 12, 16, thereby making the chamber height just slightly less than the mean separator 26 diameters. In the chamber embodiment shown in FIG. 6, the separators 26 consist of a material that has less flexibility than the first panel 12 and the second panel 16, and will overlay the separators 26 in a tent-like fashion. In this embodiment, although small local regions of the chamber 10 may deviate from the desired chamber height 20, the average height 20 of the chamber 10 will be very close to that of the mean separator 26 diameter. Analysis indicates that the mean chamber height 20 can be controlled to one percent (1%) or better at chamber heights of less than four microns using this embodiment. Referring to FIG. 5, the panel 12 that is to be vertically disposed above the other includes a plurality of ports 30 disposed at regular intervals (e.g., that act as air vents), and the panels 12, 16 are bonded together at points. In some embodiments, the bonding material 32 forms an outer chamber wall operable to laterally contain the sample 34 within the analysis chamber 10. A specific example of an acceptable separator is spheres made of polystyrene that are commercially available, for example, from Thermo Scientific of Fremont, Calif., U.S.A., catalogue no. 4204A, in four micron (4 µm) diameter.

In some applications, an isovolumetric sphering agent (e.g., a zwitterionic detergent or similarly functioning reagent) is admixed with at least a portion of the sample to cause at least some of the RBCs to assume a substantially spherical geometry. RBCs 22 in their natural faun are often bioconcave disc shaped 38 (see FIG. 1) rather than spherically shaped 40. As a result, absent the effect of the isovolumetric sphering agent, a large percentage of the disc shaped RBCs 22 will not contact both of the chamber panels 12, 16. Increasing the number of RBCs 22 that have a substantially spherical geometry will increase the number of RBCs 22 in contact with both panels 12, 16, including some cells 42 that are restrained by the chamber panels, but would otherwise be spherical. The isovolumetric sphering agent can be disposed in a discrete region of a chamber 10 (e.g., by deposition on a particular portion of an interior surface). In the absence of sample mixing within the chamber 10, the agent will only admix with the portion of the sample proximate the agent, thereby leaving other sample portions untreated by the sphering agent. This selective sparing of a portion of the RBCs 22 from isovolumetric sphering permits, as will be described below, the qualitative morphology of the RBCs 22 to be examined by image analysis as well as presentation of images to a physician for inspection for characteristics such as their roundness, their shape, and the presence of protuberances on the cell. The isovolumetric sphering does not perturb any of the quantitative analyses of the RBCs 22.

The analysis of the sample quiescently disposed within the chamber 10 is performed using an analysis device that is operable to image at least a portion of the sample and perform an analysis on the image. The image is produced in a manner that permits the optical density of sample to be determined on a per unit basis. The term "per unit basis" or "image unit" means a defined incremental unit of which the image of the sample can be dissected. A pixel, which is generally defined as the smallest element of an image that can be individually processed within a particular imaging system, is an example of an image unit, and an image unit may also include a small number of pixels in a collective unit. The magnification of an imaging device can also be described in linear terms (e.g., microns per pixel at the focal plane), where the linear dimension is along a particular axis of an orthogonal grid applied to the image. The actual area of the sample captured by pixels (or other image units) of the sensor at the focal plane is therefore a function of the magnification factor applied by the imaging device. Hence, the magnification of the imaging device should be known or determinable. The volume associated with that pixel is therefore the area of the image per pixel times the known chamber height, since the point in the chamber that was sensed is one where the RBC extends across the entire chamber. For example if the magnification was 0.5 microns per pixel, an image occupying 200 pixels would have an area of 50 square microns, and a volume of 50 square microns times the chamber height.

Figure 8:
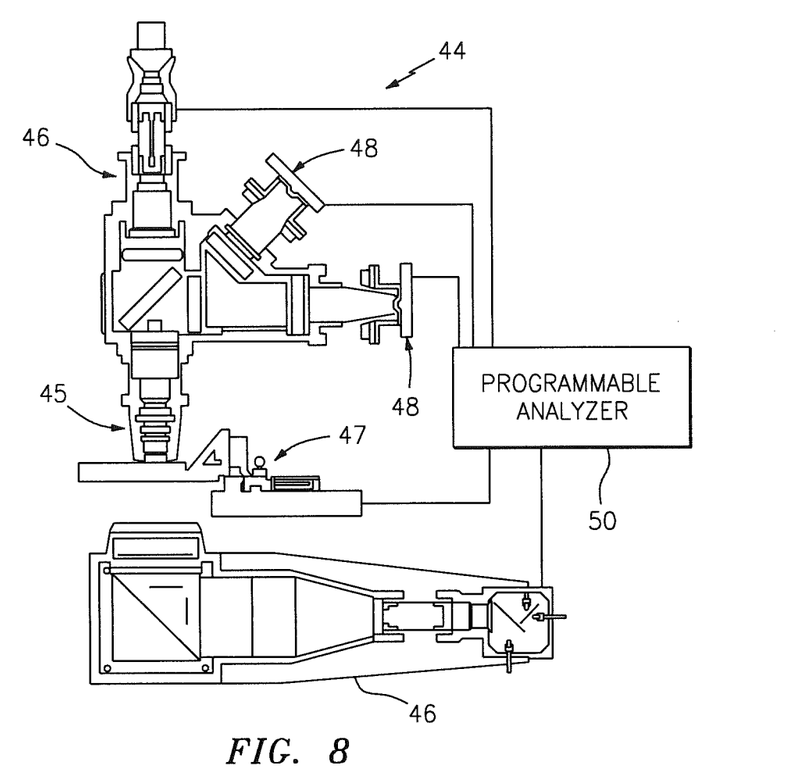
FIG. 8 is a diagrammatic schematic of an analysis device that may be used with the present method.

Now referring to FIG. 8, an example of an analysis device 44 that can be adapted for use with the present method includes an objective lens 45, a plurality of sample illuminators 46, a cartridge positioning system 47, a plurality of image dissectors 48, and a programmable analyzer 50. The sample illuminator 46 includes a light source that selectively produces light throughout a wavelength range broad enough to be useful for the hematocrit analysis (e.g., approximately 400-670 nm; light at about 413 nm and about 540 nm is particularly effective in determining the optical density of the RBCs within a sample of human blood in view of the high light absorption that occurs within the hemoglobin at the aforesaid wavelengths, which is reflected in the high molar extinction coefficient (s) at the aforesaid wavelengths), and typically includes optics for manipulating the light. The sample illuminator 46 utilizes transmittance to produce an image. The light transmission properties of the sample can be measured, for example, by positioning a light source on one side of the sample residing within the chamber 10, directing the light through the sample quiescently disposed between chamber panels, and thereafter capturing the light using the image dissector. An example of an acceptable image dissector 48 is a charge couple device (CCD) type image sensor that converts an image of the light passing through the sample into an electronic data format. Complementary metal oxide semiconductor ("CMOS") type image sensors are another example of an image sensor that can be used, and the present invention is not limited to either of these examples. The programmable analyzer 50 includes a central processing unit (CPU) and is connected to the sample illuminator 46 and image dissector 48. The CPU is adapted (e.g., programmed) to selectively perform the functions necessary to perform the present method. It should be noted that the functionality of programmable analyzer 50 may be implemented using hardware, software, firmware, or a combination thereof. A person skilled in the art would be able to program the processing unit to perform the functionality described herein without undue experimentation. U.S. Pat. No. 6,866,823 entitled "Apparatus for Analyzing Biologic Fluids" and issued Aug. 15, 2005, which is hereby incorporated by reference in its entirety, discloses such an analysis device 44.

The analysis device 44 is adapted to determine an OD value associated with the detected light signal on a per image unit basis for an imaged portion of the sample. The OD of a RBC 22 is determined by the hemoglobin concentration within the cell, the molar extinction coefficient (also referred to as molar absorptivity) for hemoglobin at a given wavelength, and the distance of the light path traveled through the hemoglobin and can be represented by the following relationship:

$$OD = \epsilon cL$$

where $\epsilon$=hemoglobin molar extinction coefficient, c=hemoglobin concentration, and L=distance traveled through the RBC 22 (i.e., the hemoglobin disposed within the cell). The molar extinction coefficient is an intrinsic property of the hemoglobin that can be can be derived by experimentation, or through empirical data currently available. As indicated above, blood naturally includes two forms of hemoglobin: deoxyhemoglobin (Hb) and oxyhemoglobin (HbO$_2$), and the value of the molar extinction coefficient for each varies as a function of wavelength, and each is different from the other with the exception of two isosbestic points (e.g., see FIG. 2). Under the present invention wherein the oxygenation state of the sample is increased until the sample is substantially oxygenated prior to analysis, the present invention advantageously permits the use of the molar extinction coefficient for oxyhemoglobin alone. As a result, the analyses for hemoglobin related parameters of whole blood samples are simplified, the potential for error is diminished, and a consequent increase in accuracy is likely.

The detected light signal (i.e., the OD values) can be used by an edge finding algorithm to identify the locations and boundaries of RBCs. RBCs 22 that contact both interior surfaces of the chamber 10 have an OD profile similar to that of a partially compressed sphere. The lateral edges of the cell 22 that are not in contact with the surfaces 14, 18 will have an OD that (in relative terms) can be considered to approach zero. The value of the determined OD: 1) increases traveling in a direction toward the center of the RBC 22 (e.g., as the light transmission path through the cell increases); 2) reaches a maximal value and remains substantially constant where the RBC is in contact with the panel interior surfaces 14, 18 (i.e., when the transmission light path through the RBC is constant); and 3) decreases traveling in a direction away from the center of the RBC 22 (e.g., as the light transmission path through the cell decreases). This characterization of the OD profile of a RBC is particularly uniform for RBCs that are spherically shaped, and is not limited to those RBCs in contact with both interior surfaces.

In some embodiments, the analysis device 44 is further adapted to determine a mean maximal OD value for a group of RBCs 22 and/or RBC aggregates 23 in contact with both interior surfaces. The determination of what constitutes an acceptable group size of RBCs and/or RBC aggregates in contact with the interior surfaces may be done on a per sample analysis basis, or it may be done periodically for "n" number of sample analyses of the same type; e.g., human blood samples. For example, a group of RBCs 22 identified as being in contact with the both interior surfaces 14, 18 can be comparatively evaluated to determine the mean maximal OD and the statistical deviation of the OD within the group. It is desirable to determine the mean maximal OD because the OD of hemoglobin within the cells 22 can vary from cell to cell even within a particular sample. If the standard deviation is greater than a predetermined threshold, a new group of RBCs 22 in contact with both panels 12, 16 can be selected, or the existing group can be expanded, until the aforesaid analysis establishes a group of RBCs 22 having a mean maximal OD with an acceptable standard deviation there from. A mean maximal OD of the RBCs 22 within a group that is about plus or minus one percent (1%) of the mean maximal OD of all the RBCs that contact both surfaces 14, 18 within the sample would, for example, be within acceptable standard deviation values. What constitutes an acceptable standard deviation value can, however, vary depending upon the application at hand and upon the specific statistical analysis being used (e.g., standard error, etc.). Existing statistical data relating to the OD of RBCs 22 is available and can be used in the determination of acceptable OD statistical values. The determination of whether the RBCs within a particular group have a mean maximal OD that is within a clinically acceptable standard deviation can also be adaptive since, as indicated above, it is well known that the population of RBCs within an individual typically have small variations in concentration of hemoglobin and a running standard deviation of the result can be used to determine how many cells must be examined before a mean of acceptable accuracy is obtained; e.g., for samples from a subject having normal blood characteristics, an acceptable group size can be as few as 100 RBCs, whereas samples from a subject having abnormal blood characteristics may require the analysis of 1000 or more RBCs. The specific number of RBCs 22 and/or RBC aggregates 23 in contact with both interior surfaces that are used to establish an acceptable mean maximal OD is not limited to any particular number or percentage of the RBCs 22 and/or RBC aggregates 23 within a sample, and may include all (e.g., thousands) of the RBCs 22 and/or RBC aggregates 23 in contact with both surfaces 14, 18.

Figure 9:
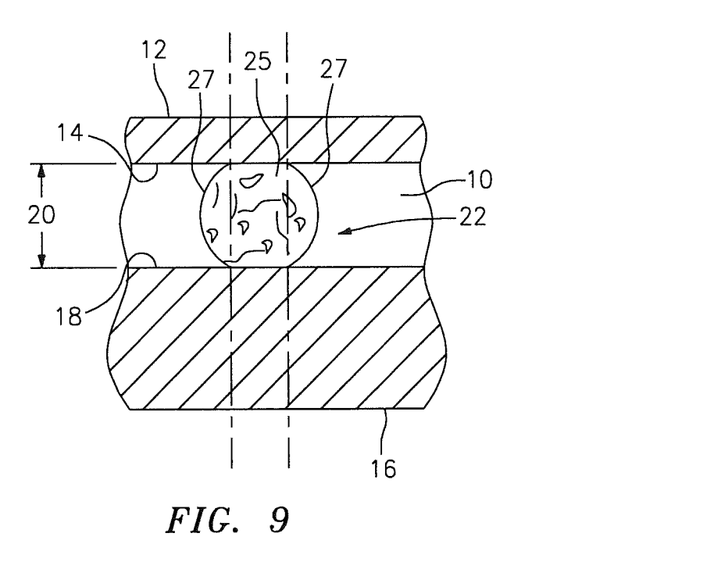
FIG. 9 is an enlarged view of a portion of the analysis chamber shown in FIG. 3.
Figure 10:
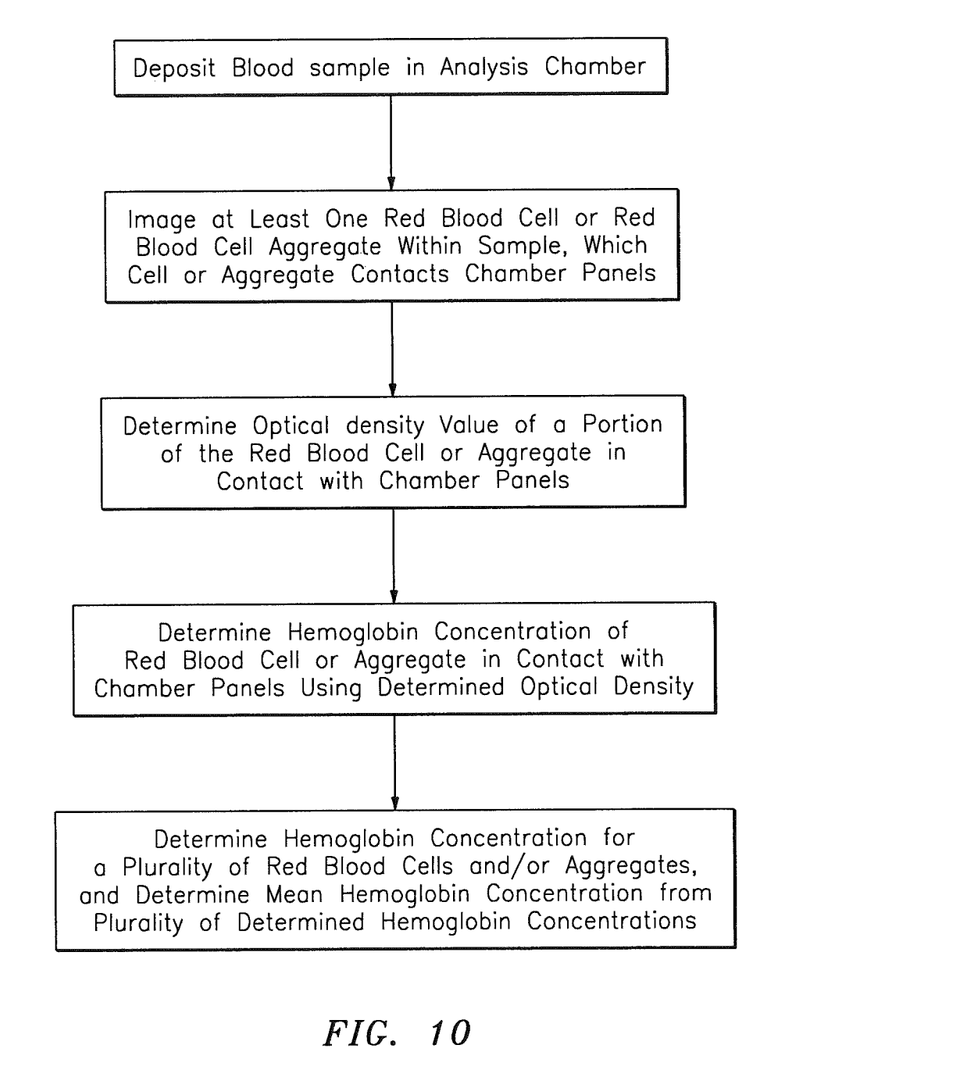
FIG. 10 is a block diagram illustrating method steps for determining the hemoglobin concentration within a red blood cell, and the mean hemoglobin concentration within a plurality of red blood cells according to an aspect of the present invention.

Now referring to FIGS. 9 and 10, the analysis device 44 is further adapted to determine the hemoglobin concentration ("CHC") of an RBC 22 by examining a portion 25 of a RBC 22 in contact with both interior surfaces 14, 18 of the chamber 10. The concentration of hemoglobin is uniform within any given RBC 22. The OD value is determined on a per pixel (or other image unit) basis. The OD signal per pixel is representative of the OD signal attributable to the height "L" of the chamber portion "aligned" with that pixel. In the determination of the CHC, the OD is sensed, the height of the chamber is either known or is determinable, and the Hemoglobin molar extinction coefficient ($\epsilon$) is known. Therefore, the CHC is determined using the relationship between optical density (OD), the hemoglobin extinction coefficient ($\epsilon$), and the length of the path through the hemoglobin (L), which for a portion 25 of a RBC 22 in contact with the interior surfaces of the chamber is equal to the height of the chamber:

$$OD = \epsilon c L, \quad c = OD/\epsilon L.$$

The mean cell hemoglobin concentration ("MCHC") of an RBC 22 is determined using the same methodology described above for determining the CHC of an individual RBC, repeated for some number of RBCs in contact with both interior surfaces of the chamber, using the results to determine a mean and an acceptable standard deviation.

Figure 11:
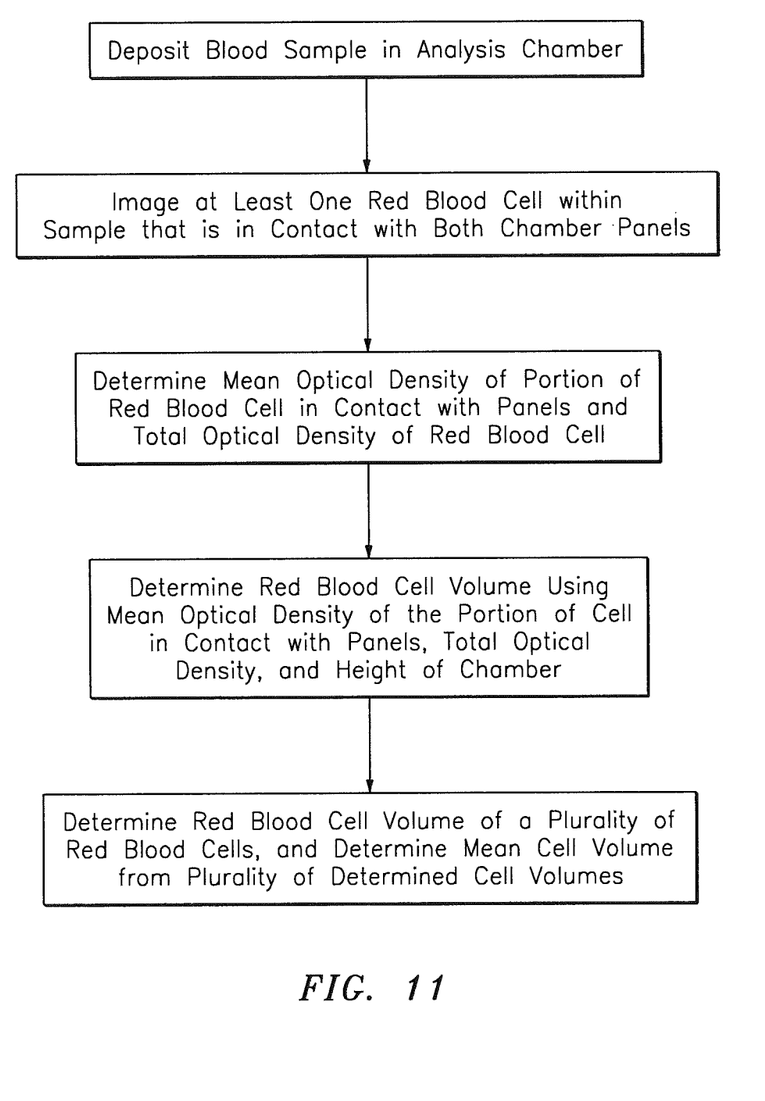
FIG. 11 is a block diagram illustrating method steps for determining the cell volume of a red blood cell, and the mean cell volume of a population of red blood cells according to an aspect of the present invention.

Now referring to FIGS. 9 and 11, the analysis device 44 is further adapted to determine the cell volume ("CV") of an individual RBC 22 in contact with both interior surfaces of the chamber 10 by integrating the volume of the RBC as a function of the OD of the hemoglobin within the RBC. The integration of the volume can be performed using a variety of analytical techniques. For example, according to a first technique, the cell volume of an individual RBC 22 in contact with both interior surfaces 14, 18 can be determined using the chamber height 20, the mean maximal optical density determined for the portion 25 of the imaged RBC 22 contacting both interior surfaces 14, 18, and the optical density determined for the entire imaged RBC 22. The total optical density of the imaged RBC is divided by the mean maximal optical density, and the result is corrected for the chamber height. According to another technique, the cell volume is determined by dividing the individual RBC 22 into different portions: the portion 25 that contacts both surfaces ("Region I"), and a portion 27 that does not contact both or even one of the interior surfaces 14, 18 ("Region II"). The volume of the cell portion 25 in contact with the interior surfaces 14, 18 is determined by sensing the OD of that portion 25 (i.e., Region I). The OD is sensed and is defined on a per pixel (or other image unit) basis. The chamber area represented by the pixel is determined, as stated above, by the size of the image per pixel which is a function of the magnification factor of the instrument. The volume associated with that pixel is therefore the area of the image per pixel times the known chamber height, since the point in the chamber that was sensed is one where the RBC 22 extends across the entire chamber height 20. The volume of the RBC portion 25 in touch with both surfaces 14, 18 (i.e., Region I) is determined by summing the volumes associated with each pixel within the two-surface contact area. The volume of the portion 27 of the RBC 22 not in contact with both surfaces 14, 18 (i.e., Region II) is determined in a similar manner. The OD value determined for the two-surface contact area is compared against the OD value for each pixel within the portion 27 of the RBC 22 not in contact with both surfaces 14, 18 (i.e., Region II). Since the hemoglobin molar extinction coefficient ($\epsilon$) is a linear function, the relative OD value of each pixel within Region II also represents the height of the RBC 22 associated with that pixel; e.g., if the OD for that pixel is 50% of the OD in Region I, the height of the RBC 22 at that point is 50% of the height of the RBC in Region I (i.e., the chamber height 20). The volume associated with each pixel in Region II is determined on a per pixel basis as described above and summed to determine the volume in Region II of the RBC 22. The volume of the RBC 22 is the sum of Regions I and II. Decreasing the area of the image on each pixel (i.e., increasing the resolution), increases the accuracy of the cell volume determination. These techniques are provided as examples of operable techniques, and the present method is not limited to these techniques.

The aforesaid techniques for determining the cell volume are operable to determine the volume of the particular RBC 22 sensed for OD. Because the OD of hemoglobin within RBCs 22 can vary from RBC to RBC even within a particular sample, determining the volume of the cell 22 using the OD sensed for that particular cell increases the accuracy of the volume determination. Many RBCs 22 do not, however, contact both interior surfaces 14, 18 of the chamber 10. For those RBCs 22 not contacting both surfaces, the cell volume can be determined using the previously obtained mean maximal optical density of the RBCs 22 that are in contact with both surfaces 14, 18. The mean maximal optical density obtained as described is sufficiently accurate to provide an accurate volume of those other cells 22. As a further alternative, for those embodiments of the present invention that utilize an isovolumetric sphering agent, the cell volume for a RBC fragment or an RBC 22 that does not contact both interior surfaces 14, 18 can also be determined by assuming the aforesaid RBC fragment or RBC is spherical. If the perimeter of the RBC 22 can be determined using a profiling technique as described above, that circular area can be used to determine the size of the sphere and therefore the volume of the RBC 22.

The analysis device 44 is further adapted to determine the mean cellular volume ("MCV") for RBCs 22 within the sample using the same methodology described above, repeated for some number of RBCs 22, using the results to determine a mean and a measure of the accuracy or confidence of the mean; e.g., an acceptable standard error of the mean. The number of RBCs 22 needed to determine a MCV with an acceptable measure of accuracy will depend on the RBC population analyzed, which number can range from about a few hundred to several thousand RBCs 22. One way of determining whether the number of RBCs whose cell volumes have been determined is an acceptable population for purposes of determining a MCV, is to iteratively determine sample mean cell volumes within the population and determine the standard error for those means; i.e., the standard deviation of the means. Once the measure of accuracy (e.g., the standard error) is within a predefined acceptable range, then the MCV is accepted.

Figure 12:
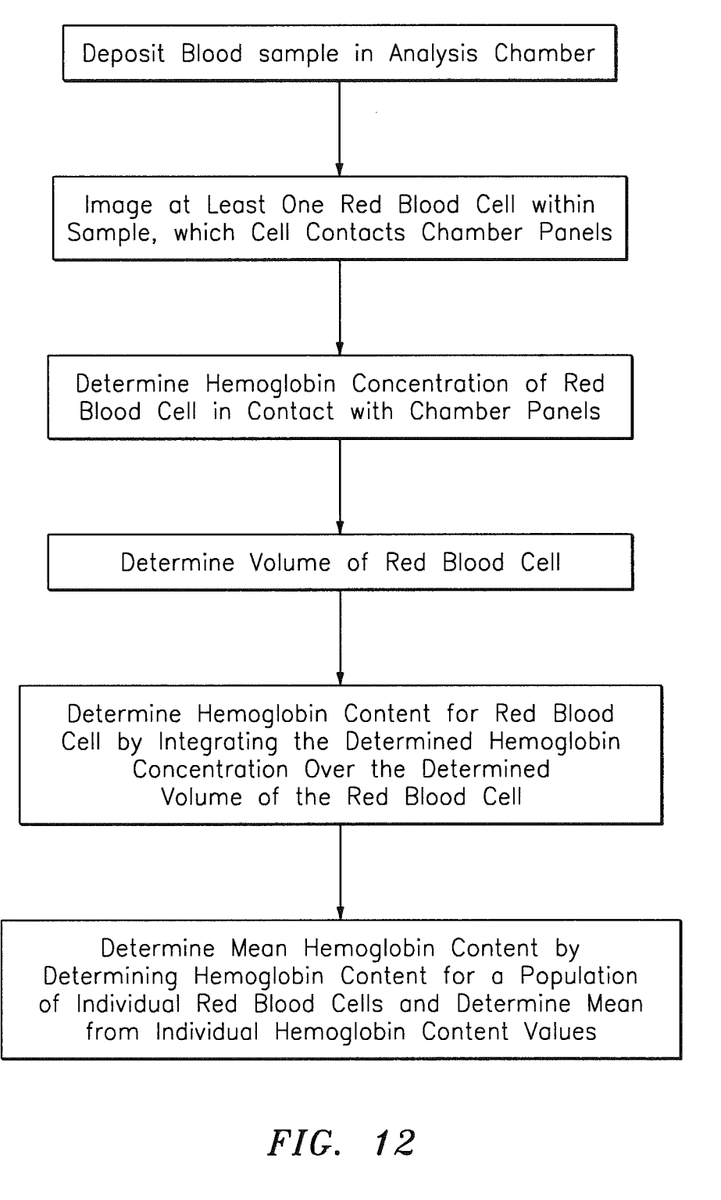
FIG. 12 is a block diagram illustrating method steps for determining the hemoglobin content of a red blood cell, and the mean hemoglobin content of a population of red blood cells according to an aspect of the present invention.

Now referring to FIGS. 9 and 12, the analysis device 44 is further adapted to determine the cell hemoglobin content ("CH") of an RBC 22 by integrating the hemoglobin concentration over the determined volume occupied by the individual RBC 22. For those RBCs 22 in contact with both interior surfaces 14, 18 of the chamber 10, the CH is determined using the determined concentration (CHC) and volume (CV) for that particular RBC 22, as is described above. If the CH is determined on an individual RBC 22 basis, then it can be done using the CHC determined for that particular RBC 22 as opposed to a mean CHC (MCHC), thereby leading to a greater degree of accuracy. For those RBCs 22 not in contact with both interior surfaces 14, 18 of the chamber 10, the CH is determined using the mean maximal optical density to determine the concentration and volume for that particular RBC 22.

The analysis device 44 is further adapted to determine the mean cell hemoglobin content ("MCH") for RBCs 22 within the sample using the same methodology described above, repeated for some number of RBCs 22, using the results to determine a mean and an acceptable measure of accuracy (e.g., standard error of the mean). The number of RBCs 22 needed to determine an MCH with an acceptable measure of accuracy will depend on the RBC population analyzed, which number can range from about a few hundred to several thousand RBCs 22. Once the measure of accuracy (e.g., the standard error) is within an acceptable range, then the MCH is accepted.

The above described methodologies for determining the CHC, MCHC, CV, MCV, CH, and MCH are examples of how these characteristics of a substantially undiluted blood sample can be determined using the described chamber and analytical device with the present invention. The present invention is not limited to these specific examples.

Under the present method, a sample of substantially undiluted whole blood is placed in a chamber 10 as is described above. An anticoagulating agent, and in some instances an isovolumetric sphering agent and/or an aggregating agent, is mixed with the sample either prior to its introduction into the chamber or upon introduction into the chamber. Reagents added in dry or semi-dry form, for example via surface coating, are particularly easy to use. The present invention is not limited to dry form reagents, however, and can for example use liquid reagents that do not meaningfully dilute the sample. The sample quiescently resides within the chamber. Under certain circumstances (e.g., very rapid analysis), it may not be necessary to add the anticoagulating agent, but it is preferable to do so in most cases to ensure the sample is in a foam acceptable for analysis. In certain analyses (e.g., those that provide information on individual RBCs), it may be preferable to not include an aggregating reagent.

At least a portion of the sample quiescently residing within the chamber 10 is imaged using the analysis device 44 by transmitting light through the sample and detecting the transmitted light. Although it is not a requirement that the entire sample residing within the chamber 10 be imaged, it is preferable since doing so typically provides a more complete analysis of the sample (and all of its constituents) and a concomitant increase in accuracy since the distribution of RBCs 22 and RBC void areas 24 within a chamber is typically non-homogeneous for a sample of substantially undiluted whole blood.

A group of RBCs 22 in contact with the interior surfaces 12, 16 of the chamber 10 is determined by the analysis device 44 using the image of the sample portion. Depending upon which characteristic of the blood sample is requested, the analysis device 44 will determine one or more of the characteristic values to arrive at the requested characteristic value.

An advantage of the present invention is that it is not necessary to have all of the RBCs 22 within the sample contact each chamber panel. The method can be performed with only some of the RBCs 22 in contact with both interior surfaces 14, 18 of the chamber 10. Smaller RBCs 22 and RBC fragments are not used to calibrate the analysis, but are measured for their contribution to the hematocrit. In addition, under the present invention the CHC, MCHC, CV, MCV, CH, and MCH of the sample can be determined without knowledge of the total area or volume of the sample within the chamber 10.

The RBCs 22 identified and analyzed under the present invention include reticulocytes (immature red blood cells), which cells develop in bone marrow as nucleated cells. Before the reticulocytes are released into circulation, they are stripped of their nuclei. The reticulocytes circulate for about a day in the blood stream before losing their reticular staining (which is a function of stained remnants of cytoplasmic RNA and nuclear DNA) and develop into mature RBCs 22 containing essentially only hemoglobin. The relative number of reticulocytes within the blood sample can be an important indicator of various conditions. For example, the number of reticulocytes is a good indicator of bone marrow red cell production activity, because it represents recent production. Abnormally absolute low numbers of reticulocytes can be indicative of aplastic anemia, pernicious anemia, bone marrow malignancies, problems of erythropoietin production, various vitamin or mineral deficiencies (B9, B12, and iron), etc. Abnormally high absolute reticulocyte counts may indicate rapid production due to the body's replacement of blood loss due to hemorrhage or hemolysis. Consequently, there is significant value in being able to detect and enumerate reticulocytes. Under the present invention, reticulocytes are identified as a RBC 22 because they contain hemoglobin, and because they can be stained to identify remaining RNA and DNA.

The reticulocytes can also be distinguished from other RBCs 22 and enumerated by admixing the sample with a stain such as a supravital dye such as acridine orange, astrozone orange, or the like. The dye causes the reticulin naturally present within the reticulocytes to fluoresce when excited by violet light at about 470 nm. The location of the RBCs 22 within the quiescent sample can be determined via the RBCs' optical density due to the contained hemoglobin in all reticulocytes and determined from the image of the sample. The reticulocytes can be distinguished from RBCs 22 not containing reticulin and from white blood cells by imaging and examining under fluorescence the sample at one or more selected wavelengths (e.g., 470 nm) associated with the supravital dye. For those RBCs identified as reticulocytes by the presence of hemoglobin and the florescence of the reticulin, the above described methodologies for determining the cell volume, cell hemoglobin content, and cell hemoglobin concentration can be used to determine the same for individual reticulocytes. In addition, statistical information (e.g., mean values and measures of accuracy) can be determined. The relative quantity of reticulin within each reticulocyte, which varies inversely with the maturity of the reticulocyte, can also be determined by the intensity of the fluorescent signal. As a result, even more specific information can be determined regarding individual reticulocytes as well as the population of reticulocytes. The relative amount of reticulin in an individual reticulocyte can be determined using either the area of fluorescence or the intensity of the fluorescence, and may be calculated as a function of the volume of an individual reticulocyte.

Using the present invention, RBC indices can also be determined including or excluding reticulocytes. For example, the MCV of a sample may be plotted both with and without including the volume contribution due to reticulocytes. Determining the MCV without reticulocytes can unmask population microcytosis that is affected by the large size of reticulocytes. Multiple other mathematical relationships among the RBCs and the reticulocytes may be determined.

As indicated above, individual indices can be determined under the present invention for RBCs 22 that do not contact both panel interior surfaces 14, 18. RBC fragments can be analyzed in the same manner, thereby permitting RBC fragments to be distinguished from other constituents found within a blood sample; e.g., platelets, platelet clumps, white cell fragments, debris, etc. The ability to detect RBC fragments using the present invention is particularly useful because RBC fragments can be indicative of conditions such as microangiopathic anemia, severe inflammation, and disseminated malignancy. The analysis of RBC fragments within a blood sample that has not been treated with an isovolumetric sphering agent can, for example, include morphological analyses to determine unaltered morphology characteristics such as size determinations, deviation from roundness, perimeter to area ratio, and the like. The OD image produced using the present invention permits the determination of characteristics such as sharpness, ellipticity, protrusions, etc., for each RBC fragment, which characteristics facilitate the aforesaid morphological analyses. Additionally, the volume of red cell fragments may be determined by measuring their diameter or circumference and calculating the volume of a sphere with those dimensions.

Although this invention has been shown and described with respect to the detailed embodiments thereof, it will be understood by those skilled in the art that various changes in form and detail may be made without departing from the spirit and scope of the invention.

What is claimed:

1. An apparatus for determining at least one hemoglobin related parameter of a whole blood sample, comprising:
   an analysis chamber, adapted to quiescently hold the whole blood sample, the chamber defined by an interior surface of a first panel, and an interior surface of a second panel, and the chamber has a height extending between the interior surfaces of the panels, wherein the chamber is configured to increase the oxygenation state of the sample to a substantially oxygenated state within a predetermined amount of time after entry into the chamber;
   an imaging unit that includes an illuminator and an image dissector, which unit is operable to image sample disposed within the chamber, and produce image signals representative of such imaged sample; and
   a programmable analyzer adapted to determine, using the image signals, at least one hemoglobin related parameter of the sample, using the image signals and a molar extinction coefficient for oxygenated hemoglobin.

2. The apparatus of claim 1, wherein the first panel of the chamber comprises a material that is oxygen permeable such that oxygen from ambient air passing through the first panel and entering the sample will increase the oxygenation state of the sample within the predetermined amount of time from prior to the determination of the hemoglobin parameter.

3. The apparatus of claim 2, wherein the first panel is a plastic film comprised of one of an acrylic, polystyrene, polyethylene terphthalate, or cyclic olefin copolymer.

4. The apparatus of claim 3, wherein the first panel has a thickness in the range of about 20-25 microns.

5. The apparatus of claim 1, wherein the first panel of the chamber comprises a material that has an oxygen solubility such that oxygen passing from within the material and entering the sample will increase the oxygenation state of the sample within the predetermined amount of time from prior to the determination of the hemoglobin parameter.

6. The apparatus of claim 1, wherein the analysis chamber has a height to width and length ratio such that the entire sample within the chamber becomes substantially oxygenated prior to the determination of the hemoglobin parameter.

7. The apparatus of claim 6, wherein the width and the length of the chamber are each at least one thousand times greater than the width.

8. The apparatus of claim 7, wherein the height of the chamber is no greater than six microns.

9. A method for determining at least one hemoglobin related parameter of a whole blood sample, comprising the steps of:
   depositing the sample into an analysis chamber adapted to quiescently hold the sample for analysis, the chamber defined by an interior surface of a first panel, and an interior surface of a second panel, and the chamber has a height extending between the interior surfaces of the panels, wherein the chamber is configured to increase the oxygenation state of the sample to a substantially oxygenated state within a predetermined amount of time after entry into the chamber;
   imaging the sample, and producing image signals;
   determining an optical density of at least a portion of the imaged sample using the image signals; and
   determining the at least one hemoglobin related parameter of the sample, using the determined optical density and a molar extinction coefficient for oxygenated hemoglobin.

10. The method of claim 9, wherein the red blood cell hemoglobin parameter is a concentration of hemoglobin.

11. The method of claim 9, wherein the first panel of the chamber comprises a material having an oxygen permeability such that oxygen passes through the first panel and enters the sample increasing the oxygenation state of the sample prior to the determination of the hemoglobin parameter.

12. The method of claim 11, wherein the first panel is a plastic film comprised of one of an acrylic, polystyrene, polyethylene terphthalate, or cyclic olefin copolymer.

13. The method of claim 12, wherein the first panel has a thickness in the range of about 20-25 microns.

14. The method of claim 9, wherein the step of depositing the sample into an analysis chamber includes depositing the sample into a chamber having a height relative to a width and a length such that the entire sample within the chamber becomes substantially oxygenated prior to the determination of the hemoglobin parameter.

15. The method of claim 9, wherein the width and the length of the chamber are each at least one thousand times greater than the width.

16. The method of claim 9, wherein the height of the chamber is no greater than six microns.

17. The method of claim 9, wherein the predetermined amount of time is equal to or less than ten seconds.

* * * * *